(12) United States Patent
Sakuramoto (10) Patent No.: US 10,520,431 B2
(45) Date of Patent: Dec. 31, 2019

(54) PARTICLE ANALYZER, PARTICLE ANALYSIS METHOD, AND PARTICLE ANALYSIS PROGRAM

(71) Applicant: HORIBA, Ltd., Kyoto-shi, Kyoto (JP)

(72) Inventor: Keijiro Sakuramoto, Kyoto (JP)

(73) Assignee: HORIBA, LTD., Kyoto (JP)

( * ) Notice: Subject to any disclaimer, the term of this patent is extended or adjusted under 35 U.S.C. 154(b) by 0 days.

(21) Appl. No.: 15/410,349

(22) Filed: Jan. 19, 2017

(65) Prior Publication Data

US 2017/0212045 A1   Jul. 27, 2017

(30) Foreign Application Priority Data

Jan. 22, 2016 (JP) ................................. 2016-011005

(51) Int. Cl.
| | | |
|---|---|---|
| *G01N 21/47* | (2006.01) | |
| *G01N 15/14* | (2006.01) | |
| *G01N 21/21* | (2006.01) | |

(52) U.S. Cl.
CPC .............. *G01N 21/47* (2013.01); *G01N 15/14* (2013.01); *G01N 21/21* (2013.01); *G01N 2021/4792* (2013.01)

(58) Field of Classification Search
CPC .... G01N 15/14; G01N 21/47; G01N 15/0205; G01N 21/51; G01N 2021/4792; G01N 21/21
See application file for complete search history.

(56) References Cited

U.S. PATENT DOCUMENTS 5,089,714 A * 2/1992 Ludlow .............. G01N 15/1456
250/574
5,548,395 A * 8/1996 Kosaka ................ G01N 15/147
356/39

(Continued)

FOREIGN PATENT DOCUMENTS

| CN | 102305757 A | 1/2012 |
| CN | 102506720 A | 6/2012 |

(Continued)

OTHER PUBLICATIONS

Search Report dated Jun. 13, 2017 from corresponding UK Patent Application No. GB 1700837.6.

(Continued)

*Primary Examiner* — Kara E. Geisel
*Assistant Examiner* — Violeta A Prieto
(74) *Attorney, Agent, or Firm* — Lucas & Mercanti, LLP (57) ABSTRACT

A particle analyzer is intended to accurately obtain an aspect ratio and a major axis length or a minor axis length of particles being dispersed in a dispersion medium. The particle analyzer includes a polarization relationship value calculation section to calculate a polarization relationship value whose parameter is light intensity of two kinds of polarization components, an aspect ratio calculation section to calculate an aspect ratio from a polarization relationship value already obtained by the polarization relationship value calculation section by using a relationship between the polarization relationship value and the aspect ratio, a diffusion coefficient acquisition section to acquire a diffusion coefficient indicating the behavior of the particles in a sample, and an axis length calculation section to calculate a major axis length from the aspect ratio already calculated by the aspect ratio calculation section and the diffusion coefficient already acquired by the diffusion coefficient acquisi- (Continued)

tion section, by using a relationship between the diffusion coefficient, the major axis length, and the aspect ratio.

6 Claims, 6 Drawing Sheets

(56) References Cited

U.S. PATENT DOCUMENTS

| | | | | |
|---|---|---|---|---|
| 8,675,195 | B2* | 3/2014 | Ihlefeld | G01N 15/0205 356/335 |
| 8,854,621 | B1* | 10/2014 | Muschol | G01N 21/47 356/336 |
| 2004/0169850 | A1* | 9/2004 | Meeks | G01B 11/0616 356/237.2 |
| 2012/0008143 | A1* | 1/2012 | Ihlefeld | G01N 15/0205 356/335 |
| 2014/0231619 | A1 | 8/2014 | Yamaguchi et al. | |
| 2015/0056710 | A1* | 2/2015 | Reed | G01N 15/0211 436/86 |
| 2016/0054343 | A1* | 2/2016 | Holmes | G01N 35/026 506/2 |
| 2016/0115027 | A1* | 4/2016 | Banin | B82Y 10/00 428/402 |

FOREIGN PATENT DOCUMENTS

| | | |
|---|---|---|
| EP | 0359681 A2 | 3/1990 |
| JP | H04-283648 A | 10/1992 |
| JP | 2009-156669 A | 7/2009 |
| JP | 2010-078468 A | 4/2010 |
| JP | 2010101877 A | 5/2010 |
| JP | 2013-205145 A | 10/2013 |
| JP | 2015-034747 A | 2/2015 |
| WO | 0014510 A1 | 3/2000 |
| WO | 2004/042371 A2 | 5/2004 |

OTHER PUBLICATIONS

JPO, Decision to Grant a Patent for corresponding Japanese patent application No.2016-011005, dated Sep. 24, 2019, with English translation (5 pages).

* cited by examiner

PARTICLE ANALYZER, PARTICLE ANALYSIS METHOD, AND PARTICLE ANALYSIS PROGRAM

CROSS REFERENCE TO RELATED APPLICATION

This Application claims the priority of Japanese Patent Application No. JP 2016-011005 filed on Jan. 22, 2016, which is incorporated herein by reference.

BACKGROUND OF THE INVENTION

Field of the Invention

The present invention relates to a particle analyzer, a particle analysis method, and a particle analysis program, which are intended to measure a ratio of a major axis length to a minor axis length (aspect ratio) in particles, and the major axis length or the minor axis length.

Background Art

As a method of analyzing a particle shape, such as a particle aspect ratio and a particle major axis length, there has conventionally been one which calculates an aspect ratio of a particle by measuring a major axis and a minor axis of the particle from an observed image obtained from a microscope.

The above microscope method needs to dry an observation object in order to measure the major axis and the minor axis of the particle. The drying of the observation object might cause a difference from the state of particles being dispersed in a liquid as a dispersion medium, and it is therefore difficult to accurately measure a particle shape in the state of being dispersed in the liquid.

Hence, as a method of analyzing the shape of particles being dispersed in the liquid, one which employs dynamic light scattering method has been proposed (refer to, for example, Patent Document 1).

The method using the dynamic light scattering method includes irradiating a vertically polarized inspection light to a measuring cell that accommodates therein a sample having particles being dispersed in a dispersion medium, and then detecting light intensity $I_{VH}$ of horizontally polarized light and light intensity $I_{VV}$ of the vertically polarized light which are contained in scattered light caused by the irradiation, with the use of a polarizing element in a photodetection section. The method also includes obtaining a rotational diffusion coefficient $\Theta$ and a translational diffusion coefficient D from an autocorrelation function of the $I_{VH}$ and an autocorrelation function of the $I_{VV}$. The $\Theta$ and the D are functions whose parameters are an aspect ratio and a major axis length, and it is therefore possible to simultaneously calculate the aspect ratio and the major axis length of the particles from the $\Theta$ and the D thus obtained.

For example, in a Perrin's relational expression for a spheroid, the $\Theta$ and the D are indicated by the following expression. In the expression, $k_B$ is Boltzmann's constant J/K, T is absolute temperature K, $\eta$ is a coefficient of viscosity kg/(m·s), a is ½ m of a major axis length, and p is a reciprocal of an aspect ratio.

$$D(a, \rho) = \frac{k_B T}{3\pi\eta a} G(\rho) \quad [\text{Expression 1}]$$

$$\Theta(a, \rho) = \frac{3k_B T}{16\pi\eta a^3} \frac{(2-\rho^2)G(\rho) - 1}{1 - \rho^4}$$

$$G(\rho) = (1-\rho^2)^{-1/2} \ln\left\{\frac{1 + (1-\rho^2)^{1/2}}{\rho}\right\}; \rho < 1$$

PRIOR ART DOCUMENT

Patent Document

Patent Document 1: Japanese Unexamined Patent Publication No. 2010-101877

SUMMARY OF THE INVENTION

Problems to be Solved by the Invention

However, both of the rotational diffusion coefficient $\Theta$ and the translational diffusion coefficient D as described above contain an error component. The aspect ratio and the major axis length obtained by using both of the rotational diffusion coefficient $\Theta$ and the translational diffusion coefficient D are affected by these error components, and therefore have unsatisfactory accuracy.

Meanwhile, as a result of an extensive investigation of the present inventor to reduce the errors of the aspect ratio and the major axis length calculated using both of the rotational diffusion coefficient $\Theta$ and the translational diffusion coefficient D, the present inventor has found that there is a certain relationship between a value whose parameters are the light intensity $I_{VH}$ of the horizontally polarized light and the light intensity $I_{VV}$ of the vertically polarized light, and the aspect ratio of particles, such as a ratio of the light intensity $I_{VH}$ and the light intensity $I_{VV}$ ($I_{VH}/I_{VV}$), and a particle aspect ratio.

Accordingly, the present invention has been made on the basis of the finding obtained from the extensive investigation of the present inventor, and has for its main object to accurately obtain an aspect ratio and a major axis length or a minor axis length of particles being dispersed in a dispersion medium.

Means of Solving the Problems

A particle analyzer of the present invention is intended for a sample having particles being dispersed in a dispersion medium, and is configured to measure an aspect ratio of a major axis length of the particles to a minor axis length thereof and measure the minor axis length or the major axis length by performing light irradiation to the sample and then detecting two different kinds of polarization components contained in scattered light to be caused by the light irradiation. The particle analyzer includes a polarization relationship value calculation section, an aspect ratio calculation section, a diffusion coefficient acquisition section, and an axis length calculation section. The polarization relationship value calculation section calculates a polarization relationship value whose parameter is light intensity of the two kinds of polarization components. The aspect ratio calculation section calculates an aspect ratio of the particles from a polarization relationship value already obtained by the polarization relationship value calculation section by using first relationship information indicating a relationship between the polarization relationship value and the aspect ratio. The diffusion coefficient acquisition section acquires a diffusion coefficient of the particles in the sample. The axis length calculation section calculates a minor axis length or a major axis length of the particles from the aspect ratio already calculated by the aspect ratio calculation section and the diffusion coefficient already acquired by the diffusion coefficient acquisition section, by using second relationship information indicating a relationship between the diffusion coefficient, either the major axis length or the minor axis length, and the aspect ratio.

Here, the polarization relationship value is, for example, one which is obtainable by using, as a parameter, light intensity ($I_{VV}$) of a polarization component (vertical polarization) at a polarizing angle 0°, and light intensity ($I_{VH}$) of a polarization component (horizontal polarization) at a polarizing angle 90°, each being contained in scattered light when vertically polarized inspection light is irradiated to the sample. Specifically, $I_{VH}/I_{VV}$, or $I_{VH}/I_{ISO}$, or the like is conceivable. Here, $I_{ISO}$ is an isotropic component of the scattered light and is represented by $I_{ISO}=I_{VV}-(3/4)\times I_{VH}$.

The second relationship information is a function of a rotational diffusion coefficient whose parameters are an aspect ratio, and a major axis length or a minor axis length, or alternatively is a function indicating a translational diffusion coefficient whose parameters are the aspect ratio, and the major axis length or the minor axis length.

With the above particle analyzer, the aspect ratio is calculated from the first relationship information indicating the relationship between the polarization relationship value whose parameter is the light intensity of the two kinds of polarization components, and the aspect ratio, and the polarization relationship value already obtained by the polarization relationship value calculation section. It is hence unnecessary to calculate the aspect ratio by using both of the rotational diffusion coefficient and the translational diffusion coefficient. This makes it possible to calculate the aspect ratio without being affected by error components of both of the rotational diffusion coefficient and the translational diffusion coefficient.

Further, the major axis length or the minor axis length is calculated from the second relationship information indicating the relationship between one kind of diffusion coefficient, the major axis length or the minor axis length, and the aspect ratio, the aspect ratio already calculated by the aspect ratio calculation section, and the diffusion coefficient already calculated by the diffusion coefficient acquisition section. It is hence unnecessary to calculate the major axis length or the minor axis length by using both of the rotational diffusion coefficient and the translational diffusion coefficient. This makes it possible to calculate the major axis length or the minor axis length without being affected by the error components of both of the rotational diffusion coefficient and the translational diffusion coefficient.

Here, the aspect ratio calculated by the aspect ratio calculation section has higher accuracy than the aspect ratio obtained using both of the rotational diffusion coefficient and the translational diffusion coefficient. Therefore, the calculation of the major axis length or the minor axis length by using the aspect ratio calculated by the aspect ratio calculation section ensures higher accuracy than the major axis length or the minor axis length obtained using both of the rotational diffusion coefficient and the translational diffusion coefficient.

As a diffusion coefficient indicating the behavior of the particles, there are the rotational diffusion coefficient and the translational diffusion coefficient. The error component contained in the rotational diffusion coefficient is larger than the error component contained in the translational diffusion coefficient.

In order to more accurately calculate the minor axis length or major axis length of the particles, the diffusion coefficient acquisition section is preferably configured to acquire a translational diffusion coefficient, and the second relationship information preferably indicates a relationship between the translational diffusion coefficient, either of the major axis length or the minor axis length, and the aspect ratio.

When the particles being dispersed in the dispersion medium correspond to an aspherical particle having a minor axis and a major axis, such as a particle having a spheroidal shape and a columnar shape, the shape of the particles can be measured accurately owing to the above configuration. The polarization relationship value determines whether or not the particles are the aspherical particles having a minor axis and a major axis.

Therefore, the particle analyzer preferably further includes a particle shape determination section to determine whether the particles are spherical particles or aspherical particles according to the polarization relationship value calculated by the polarization relationship value calculation section. When the particle shape determination section makes a determination that the particles are the aspherical particles, the aspect ratio calculation section preferably calculates an aspect ratio of the particles, and the axis length calculation section preferably calculates a minor axis length or a major axis length of the particles.

When the particles being dispersed in the dispersion medium are particles having neither a minor axis nor a major axis, or particles having substantially no difference between a minor axis and a major axis, an aspect ratio and a minor axis length or a major axis length do not necessarily need to be obtained, and it is rather advantageous for the analyzer to obtain a particle diameter.

Therefore, the particle analyzer preferably further includes a particle diameter calculation section to calculate a particle diameter of the particles when the particle shape determination section makes a determination that the particles are spherical particles.

A particle analysis method according to the present invention is intended for a sample having particles being dispersed in a dispersion medium, and is configured to measure an aspect ratio of a major axis length of the particles to a minor axis length thereof and measure the minor axis length or the major axis length by performing light irradiation to the sample and then detecting two different kinds of polarization components contained in scattered light to be caused by the light irradiation. The particle analysis method includes: a polarization relationship value calculation step of calculating a polarization relationship value whose parameter is light intensity of the two kinds of polarization components; an aspect ratio calculation step of calculating an aspect ratio of the particles from a polarization relationship value already obtained by the polarization relationship value calculation step by using first relationship information indicating a relationship between the polarization relationship value and the aspect ratio; a diffusion coefficient acquisition step of acquiring a diffusion coefficient of the particles in the sample; and an axis length calculation step of calculating a minor axis length or a major axis length of the particles from the aspect ratio already calculated by the aspect ratio calculation step and the diffusion coefficient already acquired by the diffusion coefficient acquisition step, by using second relationship information indicating a relationship between the diffusion coefficient, either the major axis length or the minor axis length, and the aspect ratio.

A particle analysis program according to the present invention is used for a particle analyzer intended for a sample having particles being dispersed in a dispersion medium and configured to measure an aspect ratio of a major axis length of the particles to a minor axis length thereof and measure the minor axis length or the major axis length by performing light irradiation to the sample and then detecting two different kinds of polarization components contained in scattered light to be caused by the light irradiation. The particle analysis program causes a computer to have functions as a polarization relationship value calculation section to calculate a polarization relationship value whose parameter is light intensity of the two kinds of polarization components, an aspect ratio calculation section to calculate an aspect ratio of the particles from a polarization relationship value already obtained by the polarization relationship value calculation section by using first relationship information indicating a relationship between the polarization relationship value and the aspect ratio, a diffusion coefficient acquisition section to acquire a diffusion coefficient of the particles in the sample, and an axis length calculation section to calculate a minor axis length or a major axis length of the particles from the aspect ratio already calculated by the aspect ratio calculation section and the diffusion coefficient already acquired by the diffusion coefficient acquisition section, by using second relationship information indicating a relationship between the diffusion coefficient, either the major axis length or the minor axis length, and the aspect ratio.

Effects of the Invention

With the present invention thus configured, there is no need to calculate the aspect ratio and the major axis length or the minor axis length by using both of the rotational diffusion coefficient and the translational diffusion coefficient. This makes it possible to accurately obtain the aspect ratio and the major axis length or the minor axis length of the particles being dispersed in the dispersion medium.

DESCRIPTION OF THE EMBODIMENTS

One embodiment of a particle analyzer according to the present invention is described below with reference to the drawings.

The particle analyzer 100 of the present embodiment is intended to analyze a shape of an aspherical particle (particle having anisotropy) having a minor axis and a major axis, such as a spheroidal shape and a columnar shape.

Figure 1:
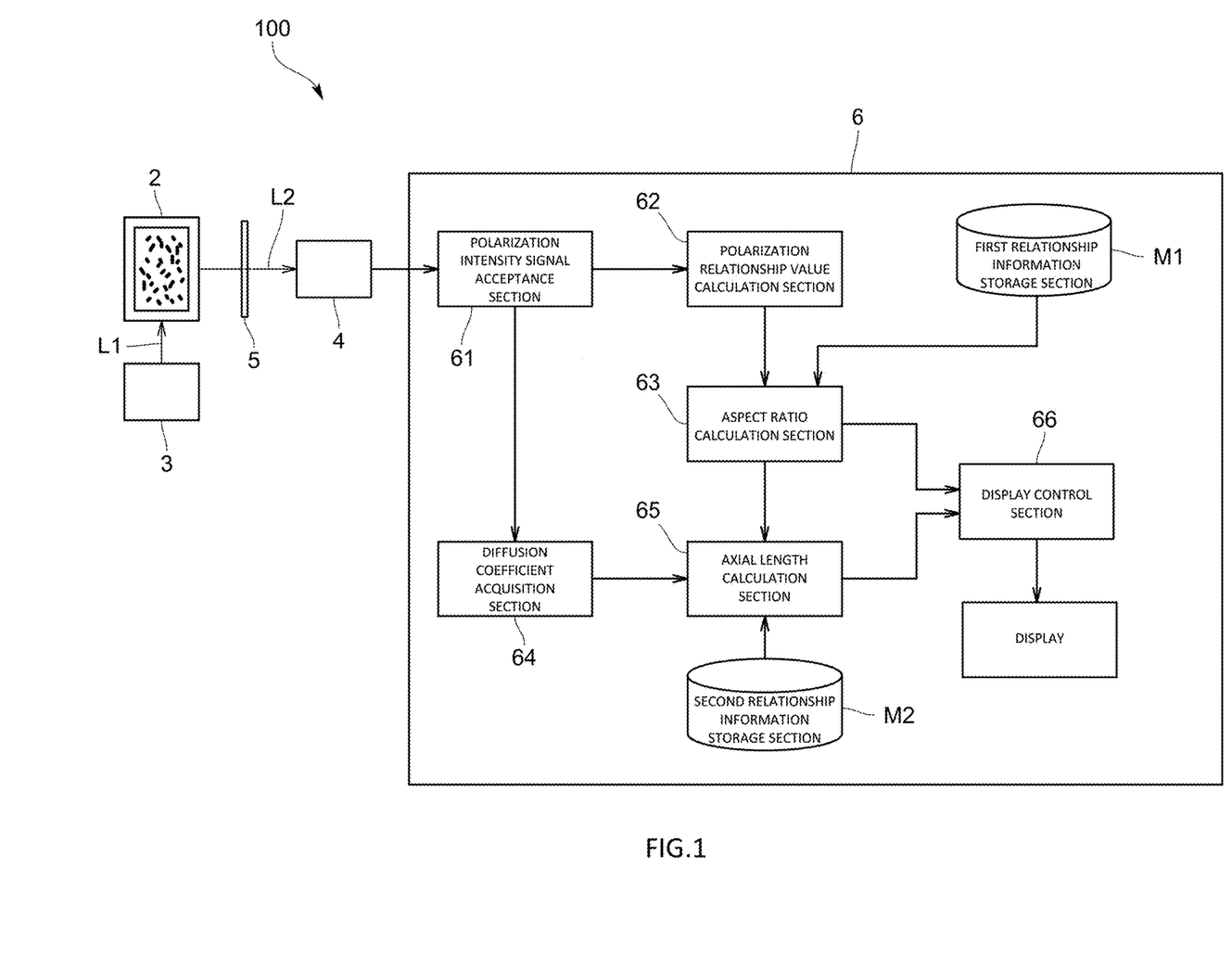
FIG. 1 is a schematic diagram that shows an overall configuration of a particle analyzer of an embodiment.

To be specific, as shown in FIG. 1, the particle analyzer 100 includes a measuring cell 2 to accommodate therein a liquid sample having aspherical particles being dispersed in a liquid as a dispersion medium, a laser light source 3 to irradiate laser light L1 as being inspection light to the measuring cell 2, a photodetector 4 to detect scattered light L2 to be emitted from the particles after being subjected to the irradiation of the laser light L1, a polarizing element 5 that is disposed between the measuring cell 2 and the photodetector 4 and permits transmission of a predetermined polarization component contained in the scattered light L2, and an information processor 6 to calculate an aspect ratio (major axis length/minor axis length) and the major axis length of the particles by acquiring a light intensity signal obtained by the photodetector 4.

Figure 2:
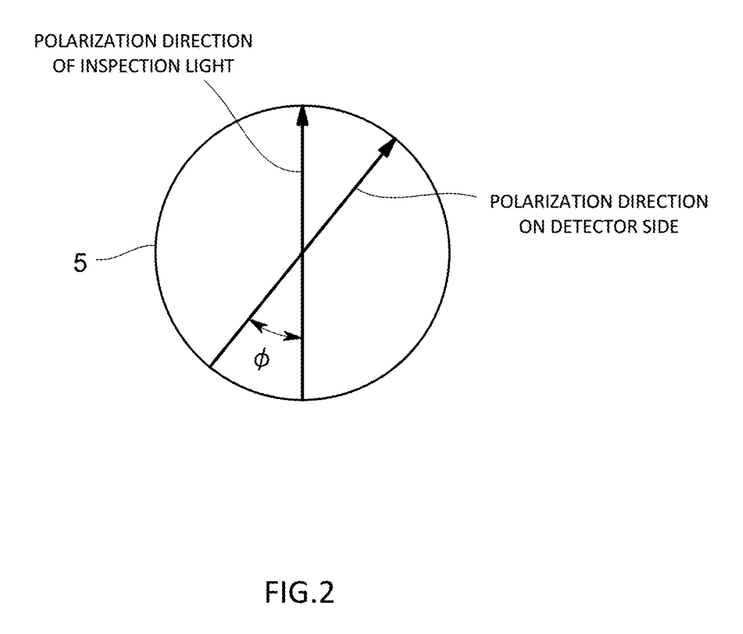
FIG. 2 is a diagram that shows a polarization direction of inspection light and an angle of a polarizing element in the embodiment.

In the present embodiment, the inspection light L1 to be irradiated to the measuring cell 2 is a vertical polarization component as shown in FIG. 2. The polarizing element 5 is disposed tiltably with respect to the vertical polarization component so that a polarization component at a desired polarizing angle $\phi$ is detectable by the photodetector 4.

For example, by setting $\phi=0°$, a light intensity signal $I_{VV}$ of the vertical polarization component is detectable by the photodetector 4. By setting $\phi=90°$, a light intensity signal $I_{VH}$ of the horizontal polarization component is detectable by the photodetector 4.

The information processor 6 of the present embodiment is a dedicated or general purpose computer including a CPU, a memory, an input/output interface, an AD convertor, input means such as a keyboard, and display means such as a display. The information processor 6 performs controls of sections necessary for a particle analysis, such as polarizing angle control of the polarizing element 5, according to a particle analysis program stored in the memory. The information processor 6 also conducts functions, such as a polarization intensity signal acceptance section 61, a polarization relationship value calculation section 62, a first relationship information storage section M1, an aspect ratio calculation section 63, a diffusion coefficient acquisition section 64, a second relationship information storage section M2, an axis length calculation section 65, and a display control section 66, as shown in FIG. 1. These sections are described in detail below.

The polarization intensity signal acceptance section 61 is configured to acquire two different kinds of polarization components from the photodetector 4.

Specifically, the polarization intensity signal acceptance section 61 acquires the light intensity signal $I_{VV}$ of the vertical polarization component when the polarizing angle $\phi$ of the polarizing element 5 is 0°, and acquires the light intensity signal $I_{VH}$ of the horizontal polarization component when the polarizing angle $\phi$ of the polarizing element 5 is 90°. When the polarizing angle $\phi$ of the polarizing element 5 is an angle other than 0° or 90°, the polarization intensity signal acceptance section 61 is also capable of acquiring a light intensity signal of a polarization component at the polarizing angle $\phi$.

The polarization relationship value calculation section 62 is configured to calculate a polarization relationship value whose parameters are the light intensity signal $I_{VV}$ of the vertical polarization component and the light intensity signal $I_{VH}$ of the horizontal polarization component which are already acquired by the polarization intensity signal acceptance section 61.

Specifically, the polarization relationship value calculation section 62 calculates, as a polarization relationship value, $I_{VH}/I_{ISO}$, in which $I_{ISO}$ is an isotropic component of scattered light and is represented by $I_{ISO}=I_{VV}-(3/4)\times I_{VH}$.

The first relationship information storage section M1 stores therein first relationship information data indicating a relationship between the polarization relationship value $(I_{VH}/I_{ISO})$ and an aspect ratio.

Figure 3:
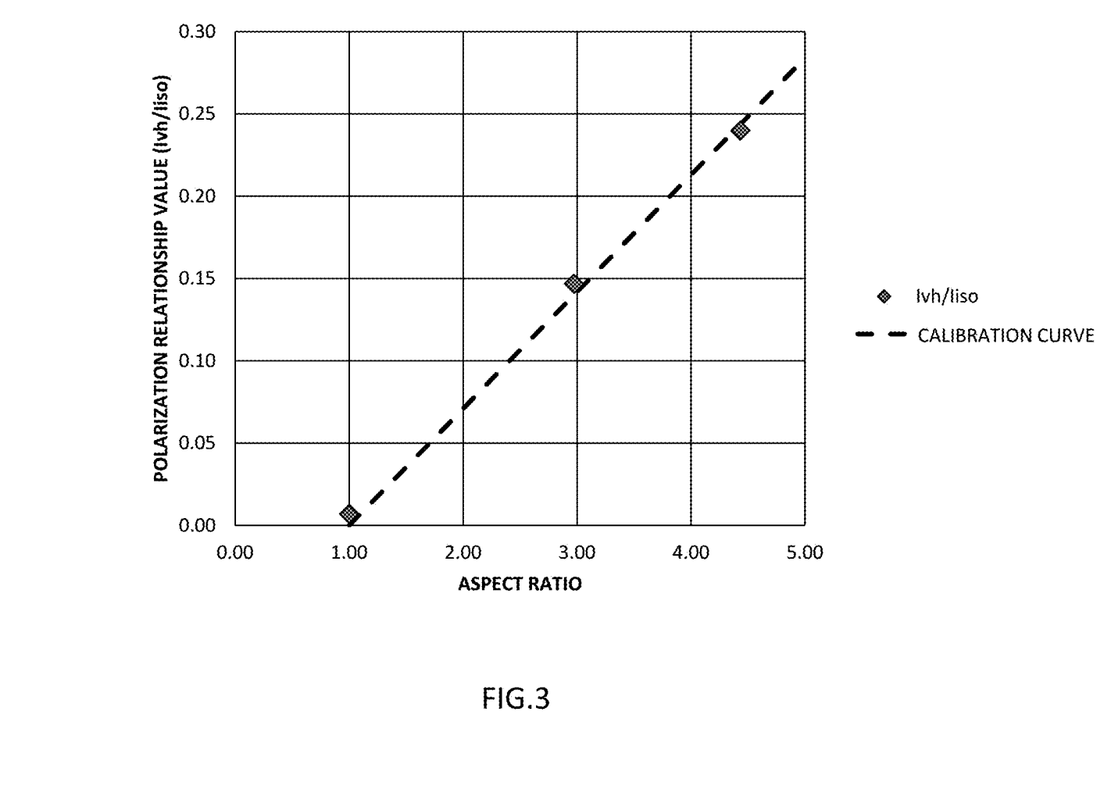
FIG. 3 is a graph that shows a relationship between a polarization relationship value and an aspect ratio.

The first relationship information data are obtainable in advance by using a standard particle having a known aspect ratio, and are data of a relational expression (calibration curve) indicating a relationship between the polarization relationship value $(I_{VH}/I_{ISO})$ and the aspect ratio, as shown in FIG. 3. Alternatively, the first relationship information data may be data of a relationship table that indicates a relationship between the polarization relationship value $(I_{VH}/I_{ISO})$ and the aspect ratio.

The first relationship information data may be those which are inputted through input means, such as a keyboard, or alternatively those which are inputted through an external memory, such as a USB memory and an SD card, or still alternatively those which are inputted through a wireless or wired communication, such as internet.

The aspect ratio calculation section 63 is configured to acquire the first relationship information data from the first relationship information storage section M1, and the polarization relationship value data indicating the polarization relationship value calculated by the polarization relationship value calculation section 62, and is configured to calculate an aspect ratio from these acquired data.

The diffusion coefficient acquisition section 64 is configured to acquire a diffusion coefficient that indicates the behavior of particles in a liquid sample. In the present embodiment, the diffusion coefficient acquisition section 64 is configured to calculate a diffusion coefficient by using the light intensity signal $I_{VV}$ of the vertical polarization component and the light intensity signal $I_{VH}$ of the horizontal polarization component which are already acquired by the polarization intensity signal acceptance section 61.

Figure 4:
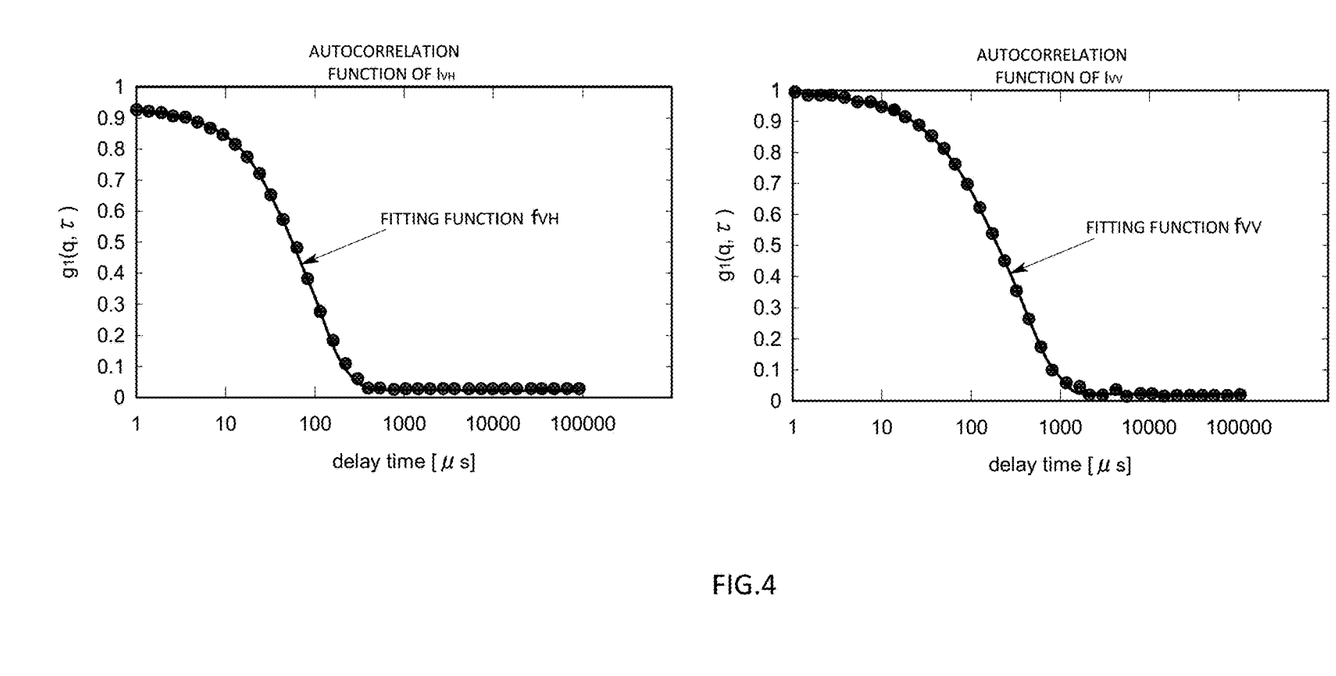
FIG. 4 is a graph that shows an autocorrelation function in light intensity of a horizontal polarization component and an autocorrelation function in light intensity of a vertical polarization component.

Specifically, as shown in FIG. 4, the diffusion coefficient acquisition section 64 calculates an autocorrelation function of the light intensity signal $I_{VV}$ of the vertical polarization component, and calculates an autocorrelation function of the light intensity signal $I_{VH}$ of the horizontal polarization component. The diffusion coefficient acquisition section 64 obtains a rotational diffusion coefficient $\Theta$ and a translational diffusion coefficient D by using a fitting function $f_{VH}$ (q, $\tau$) with respect to the autocorrelation function of the $I_{VH}$ and a fitting function $F_{VV}$ (q, $\tau$) with respect to the autocorrelation function of the $I_{VV}$, and then respectively changing their coefficients a1 to a3, and b1, followed by fitting. Here, the $f_{VH}$ (q, $\tau$) and the $F_{VV}$ (q, $\tau$) are as follows.

$$f_{VH}(q,\tau)=a_1 \exp(-b_1\tau)(b_1=q^2 D+6\Theta)$$

$$f_{VV}(q,\tau)=a_2 \exp[-(b_1-6\Theta)\tau]+a_3 \exp(-b_1\tau) \quad \text{[Expression 2]}$$

The second relationship information storage section M2 stores therein second relationship information data indicating a relationship between the translational diffusion coefficient D, the major axis length, and the aspect ratio.

Here, the second relationship information data are data of a function that indicates the translational diffusion coefficient D whose parameters are the aspect ratio and the major axis length. The function D (a, $\rho$) that indicates the translational diffusion coefficient of the present embodiment is the Perrin's relational expression for a spheroid, and is represented by the following expression, in which $k_B$ is Boltzmann constant J/K, T is absolute temperature K, $\eta$ is a coefficient of viscosity kg/(m·s), a is ½ m of a major axis length, and $\rho$ is a reciprocal of an aspect ratio.

$$D(a, \rho) = \frac{k_B T}{3\pi\eta a} G(\rho) \quad \text{[Expression 3]}$$

$$G(\rho) = (1-\rho^2)^{-1/2} \ln\left\{\frac{1+(1-\rho^2)^{1/2}}{\rho}\right\}; \rho < 1$$

The second relationship information data may be those which are inputted through input means, such as a keyboard, or alternatively those which are inputted through an external memory, such as a USB memory and an SD card, or still alternatively those which are inputted through a wireless or wired communication, such as internet.

The axis length calculation section 65 acquires the second relationship information data from the second relationship information storage section M2, acquires the aspect ratio data indicating the aspect ratio calculated by the aspect ratio calculation section 63, and acquires the translational diffusion coefficient data indicating the translational diffusion coefficient D calculated by the diffusion coefficient acquisition section 64. The axis length calculation section 65 calculates a particle major axis length from these data. The axis length calculation section 65 is also capable of calculating a minor axis length from the aspect ratio and the major axis length.

The display control section 66 is configured to acquire the data calculated by the calculation sections or acquisition sections 62 to 65 and performs a screen display of these data on display means, such as a display. Besides this, the display control section 66 performs a screen display necessary for the particle analysis in the particle analyzer 100.

With the particle analyzer 100 thus configured according to the present embodiment, the aspect ratio is calculated from the first relationship information indicating the relationship between the polarization relationship value $(I_{VH}/I_{ISO})$ and the aspect ratio, and the polarization relationship value $(I_{VH}/I_{ISO})$ already obtained by the polarization relationship value calculation section 62, and it is hence unnecessary to calculate the aspect ratio by using both of the rotational diffusion coefficient $\Theta$ and the translational diffusion coefficient D. This makes it possible to calculate the aspect ratio without being affected by the error components of both of the rotational diffusion coefficient $\Theta$ and the translational diffusion coefficient D.

The major axis length is calculated from the second relationship information indicating the relationship between the translational diffusion coefficient D, the major axis length, and the aspect ratio, the aspect ratio already calculated from the aspect ratio calculation section 63, and the translational diffusion coefficient D already obtained by the diffusion coefficient acquisition section 64, and it is hence unnecessary to calculate the major axis length or the minor axis length by using both of the rotational diffusion coefficient $\Theta$ and the translational diffusion coefficient D. This makes it possible to calculate the major axis length without being affected by the error components of both of the rotational diffusion coefficient $\Theta$ and the translational diffusion coefficient D. Particularly, the present embodiment uses the translational diffusion coefficient D with a small error component without using the rotational diffusion coefficient Θ with a large error component, thus leading to an accurate calculation of the major axis length.

Here, the aspect ratio calculated by the aspect ratio calculation section 63 is more accurate than the aspect ratio obtained using both of the rotational diffusion coefficient Θ and the translational diffusion coefficient D. Therefore, the calculation of the major axis length using the aspect ratio calculated by the aspect ratio calculation section 63 ensures higher accuracy than the major axis length obtained using both of the rotational diffusion coefficient Θ and the translational diffusion coefficient D.

Specifically, the aspect ratio obtained with the conventional method using both of the rotational diffusion coefficient Θ and the translational diffusion coefficient D was 1.83, whose relative error with respect to one which was measured with a transmission electron microscope (TEM) was 59%. The major axis length obtained with the conventional method was 133.6 nm, whose relative error with the respect one which was measured with the TEM was 31%.

In contrast, the aspect ratio obtained with the method of the present embodiment using the polarization relationship value—aspect ratio relational expression was 4.43, whose relative error with respect to one which was measured with the TEM was 1%. The major axis length obtained with the method of the present embodiment was 204.1 nm, whose relative error with respect to one which was measured with the TEM was 5%. Thus, the aspect ratio and the major axis length are accurately measurable with the particle analyzer 100 of the present embodiment.

It should be noted that the present invention is not limited to the above embodiment.

For example, the above embodiment is directed to one which calculates the major axis length or the minor axis length by using the translational diffusion coefficient D, or alternatively may be one which calculates the major axis length or the minor axis length by using the rotational diffusion coefficient Θ. In this alternative, the second relationship information storage section M2 stores therein second relationship information data indicating a relationship between the rotational diffusion coefficient Θ, the major axis length, and the aspect ratio.

The major axis length obtained in this alternative was 170.1 nm, whose relative error with respect to one which was measured with the TEM was 13%. Even in the case of obtaining the major axis length by using the rotational diffusion coefficient Θ, it is possible to more accurately measure the major axis length than the conventional method using both of the rotational diffusion coefficient Θ and the translational diffusion coefficient D.

Alternatively, the second relationship information data may be data indicating a relationship between the rotational diffusion coefficient Θ or the translational diffusion coefficient D, the aspect ratio, and the minor axis length.

Although the polarization relationship value in the present embodiment is $I_{VH}/I_{ISO}$, no particular limitation is imposed thereon as long as it is one whose parameters are two different kinds of polarization components, such as $I_{VH}/I_{VV}$. In this alternative, it is necessary to prepare in advance the first relationship information indicating a relationship between a polarization relationship value thereof and the aspect ratio.

Moreover in the above embodiment, the two different kinds of polarization components are the polarization component of $\phi=0°$ and the polarization component of $\phi=90°$, the combination of the polarization components is not limited thereto, and another polarization component (for example, a polarization component of $\phi=45°$) may be used. In this alternative, it is necessary to prepare in advance first relationship information indicating a relationship between a polarization relationship value obtainable using the another polarization component (for example, $\phi=45°$), and the aspect ratio.

The diffusion coefficient acquisition section 64 of the above embodiment is one which calculates the diffusion coefficient by using the light intensity signals $I_{VV}$ and $I_{VH}$ of the two kinds of polarization components, or alternatively may be one which calculates the rotational diffusion coefficient Θ and the translational diffusion coefficient D by using light intensity signals of three or more kinds of polarization components whose polarizing angles are different from one another. Thus, by calculating the rotational diffusion coefficient Θ and the translational diffusion coefficient D by using the light intensity signals of the three kinds of polarization components, it is possible to reduce error components contained in the rotational diffusion coefficient Θ and the translational diffusion coefficient D, thereby making it possible to more accurately measure the major axis length or the minor axis length.

Additionally, the particle analyzer 100 of the present embodiment may be configured to verify the validity of measurement results as follows.

Specifically, the particle analyzer 100 is configured to set a plurality of polarizing angles $\phi$ of the polarizing element in a range of $0°\leq\phi<90°$, and acquire a light intensity signal of the polarization component at each of the polarizing angles $\phi$. Then, the diffusion coefficient acquisition section 64 calculates an autocorrelation function of the light intensity signal of the polarization component at each of the polarizing angles $\phi$. The diffusion coefficient acquisition section 64 also calculates a rotational diffusion coefficient Θ and a translational diffusion coefficient D by fitting the autocorrelation function obtained at each of the polarizing angles $\phi$ according to the following expression. The axis length calculation section 65 calculates a major axis length or a minor axis length by using the rotational diffusion coefficient Θ or the translational diffusion coefficient D so obtained.

$$g_1(q,\tau)=A(\phi)\exp(-b_1\tau)+B(\phi)\exp(-(b_1-6\Theta)\tau)$$
$$(b_1=q^2D+6\Theta) \qquad \text{[Expression 4]}$$

Subsequently, the diffusion coefficient acquisition section 64 outputs data of coefficients $A(\phi)$ and $B(\phi)$ at each of the polarizing angles $\phi$ obtained by the fitting, to the display control section 66.

Figure 5:
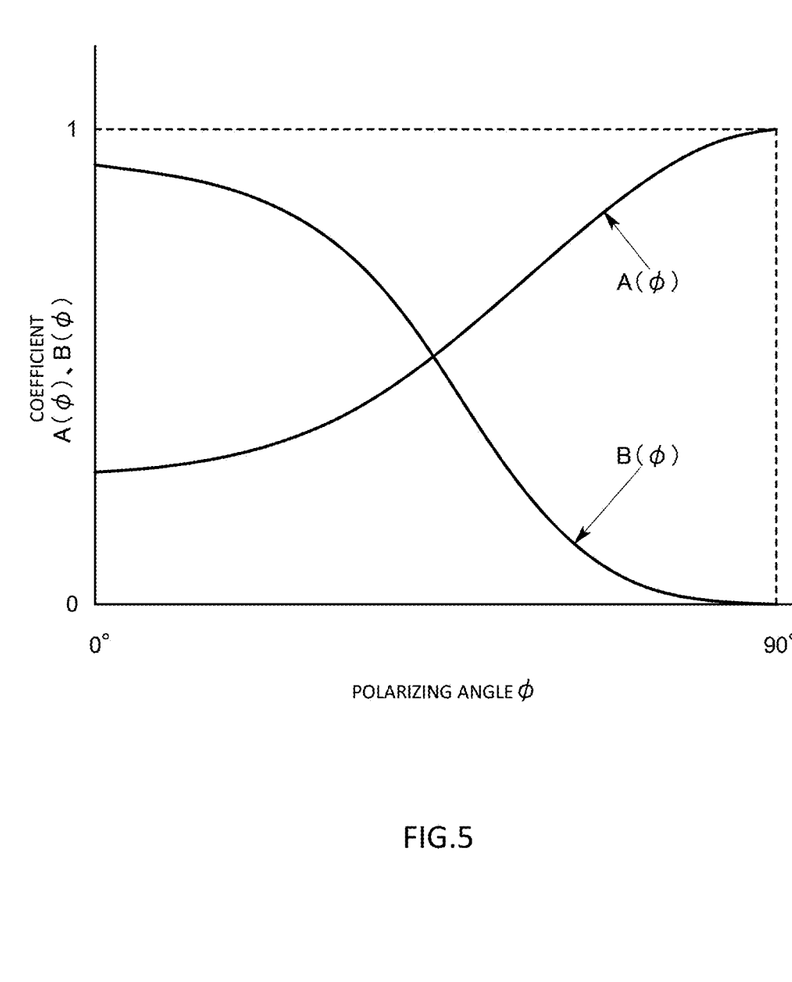
FIG. 5 is a graph that shows a coefficient of a fitting function in each polarization angle in a modified embodiment.

Upon acquisition of these data, the display control section 66 performs a graph display of the coefficients $A(\phi)$ and $B(\phi)$ at each of the polarizing angles as shown in FIG. 5. By the graph display of the coefficients $A(\phi)$ and $B(\phi)$ at each of the polarizing angles as shown in FIG. 5, it is possible to determine whether the result of the major axis length or the minor axis length obtained by the axis length calculation section 65 is valid or not. In other words, when the obtained major axis length is valid, the coefficient $A(\phi)$ increases with increasing polarizing angle $\phi$, and the coefficient $B(\phi)$ decreases with increasing polarizing angle $\phi$. Thus, by displaying dependency of the coefficients $A(\phi)$ and $B(\phi)$ with respect to the polarizing angle $\phi$, a user is capable of determining the validity of the result. Besides this, the display directed by the display control section 66 is not limited to that in FIG. 5, and the display may be made in any form as long as it indicates the dependency of the coefficients $A(\phi)$ and $B(\phi)$ with respect to the polarizing angle $\phi$. For example, a difference of the coefficient $A(\phi)$ and a difference of the coefficient B(φ) at each of the polarizing angles, or the like may be displayed.

The particle analyzer 100 of the above embodiment may be configured to change a measurement item as follows, depending on whether the particles correspond to a spherical particle or aspherical particle.

Figure 6:
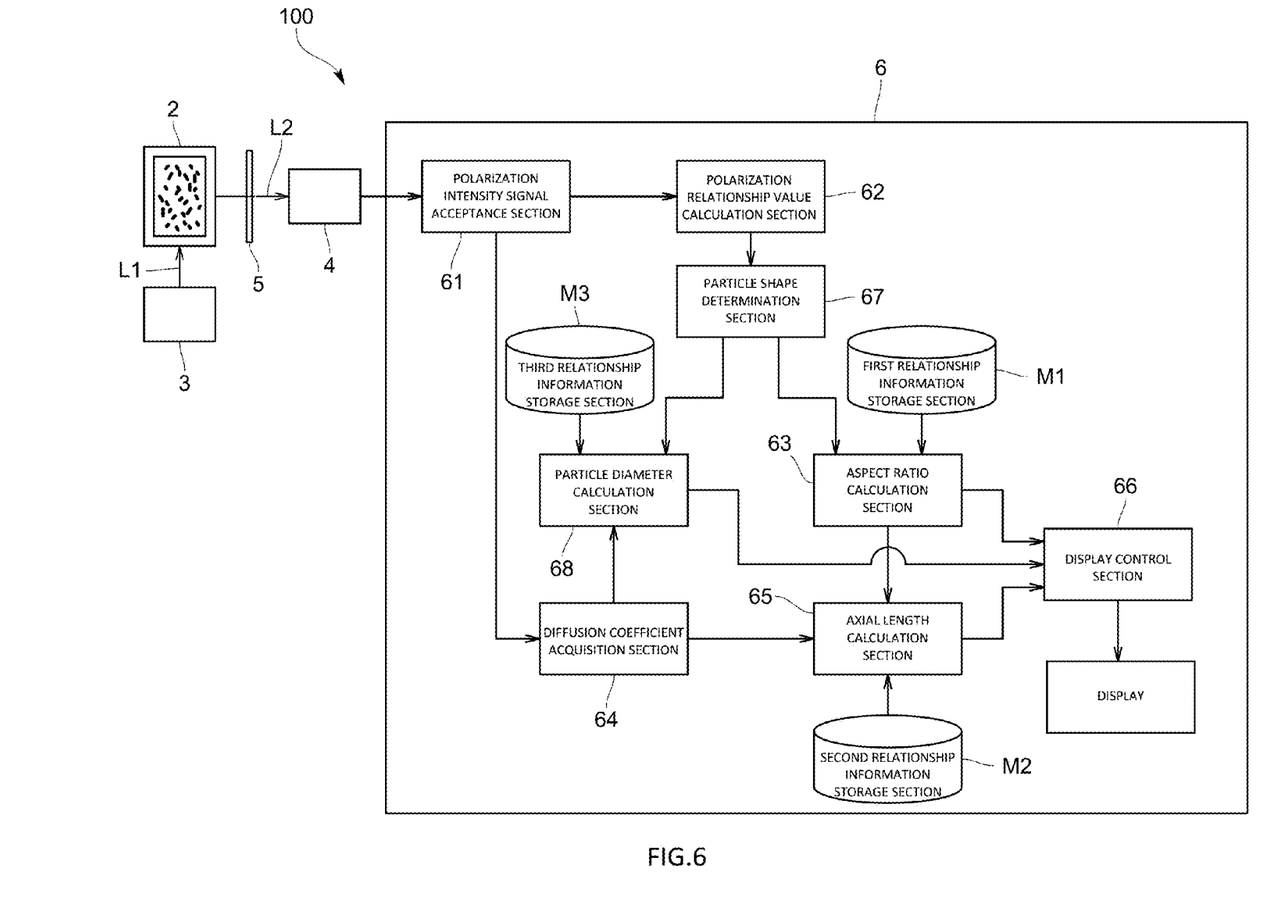
FIG. 6 is a schematic diagram that shows a general configuration of a particle analyzer of a modified embodiment.

Specifically, as shown in FIG. 6, the particle analyzer 100 may further include a particle shape determination section 67 configured to determine whether the particles correspond to a spherical particle or aspherical particle according to the polarization relationship value calculated by the polarization relationship value calculation section 62, and perform switching between the step of calculating the aspect ratio and the major axis length or the minor axis length, and the step of calculating a particle diameter, according to a determination result.

In this alternative, the particle analyzer 100 further includes a third relationship information storage section M3 to store therein third relationship information indicating a relationship between a translational diffusion coefficient D and a particle diameter, and a particle diameter calculation section 68 to calculate a particle diameter from the translational diffusion coefficient D obtained by the diffusion coefficient acquisition section 64, and the third relationship information.

Here, third relationship information data are data of a function that indicates a translational diffusion coefficient D(r) whose parameter is the particle diameter (r). The function is, for example, Stokes-Einstein relational expression, and is represented by the following expression. A method of inputting the third relationship information data is similar to that of the second relationship information data.

$$D = \frac{k_B T}{3\pi \eta r} \quad \text{[Expression 5]}$$

The particle shape determination section 67 is configured to determine whether the particles correspond to a spherical particle or aspherical particle depending on whether the polarization relationship value calculated by the polarization relationship value calculation section 62 is less than a predetermined value. With reference to FIG. 3, the particle shape determination section 67 makes a determination that the particles correspond to the spherical particle when $I_{VH}/I_{ISO}$ is less than 0.05, and makes a determination that the particles correspond to the aspherical particle when $I_{VH}/I_{ISO}$ is 0.05 or more. The particle shape determination section 67 then outputs their respective determination signals to the aspect ratio calculation section 63 and the particle diameter calculation section 68.

When the particle shape determination section 67 makes the determination that the particle is the aspherical particle, the aspect ratio calculation section 63 calculates an aspect ratio, and the axis length calculation section 65 calculates a major axis length or a minor axis length.

When the particle shape determination section 67 makes the determination that the particles correspond to the spherical particle, the particle diameter calculation section 68 calculates a particle diameter by acquiring the third relationship information data from the third relationship information storage section M3, and acquiring the translational diffusion coefficient data indicating the translational diffusion coefficient D calculated by the diffusion coefficient acquisition section 64.

Furthermore, though the diffusion coefficient acquisition section 64 of the above embodiment is configured to calculate the diffusion coefficient by acquiring intensity signals of the two kinds of polarization components from the polarization intensity signal acceptance section 61, the diffusion coefficient acquisition section 64 may be configured to acquire a translational diffusion coefficient D obtainable from a moving image when laser beam is irradiated to the liquid sample. The translational diffusion coefficient D is represented by $D=\langle\Delta r^2\rangle/2t$, in which t is time, and $\langle\Delta r^2\rangle$ is mean-square displacement at time t. Here, the diffusion coefficient acquisition section 64 may be configured to acquire a translational diffusion coefficient D calculated by an apparatus other than the particle analyzer 100, or alternatively may be configured to acquire the moving image and calculate a translational diffusion coefficient from the moving image. Thus, by obtaining the translational diffusion coefficient D from the moving image, it is possible to obtain the translational diffusion coefficient D whose error component is less than the case of obtaining it together with the rotational diffusion coefficient Θ by using the fitting function as in the above embodiment.

Although the sample in the present embodiment is the liquid sample using the liquid as the dispersion medium, it may be a sample having particles being dispersed in a dispersion medium other than the liquid, such as a gel or gas.

Besides the above, it will be understood that the present invention is not limited to the above-described embodiment, and various modifications may be made without departing from the spirit and scope of the present invention.

DESCRIPTION OF REFERENCE NUMERAL

100 particle analyzer
2 measuring cell
3 light irradiation section
4 light detection section
5 polarizing element
6 information processor
M1 first relationship information storage section
M2 second relationship information storage section
61 polarization intensity signal acceptance section
62 polarization relationship value calculation section
63 aspect ratio calculation section
64 diffusion coefficient acquisition section
65 axis length calculation section
66 display control section
M3 third relationship information storage section
67 particle shape determination section
68 particle diameter calculation section

What is claimed is:

1. A particle analyzer, comprising:
   a light source configured to irradiate light to a sample having particles being dispersed in a dispersion medium, a polarizing element and a detector, the polarizing element and the detector being configured to detect two different polarization components contained in scattered light to be caused by the light irradiation, and an information processor comprising:
   a polarization relationship value calculation section to calculate a polarization relationship value whose parameter is light intensity of the two polarization components;
   wherein the polarization relationship value calculation section is configured to obtain a first relationship information indicating a relationship between the polarization relationship value and an aspect ratio of a major axis length of the particles to a minor axis length thereof by one of calculating the first relationship information using a standard particle having a known aspect ratio, wherein the polarization relationship value of the known aspect ratio is calculated using the two different polarization components of the standard particle obtained using the light source, the polarizing element, and the detector, or obtaining the first relationship information through an external device;

a first relationship information storage section storing the previously determined first relationship information;

an aspect ratio calculation section to calculate the aspect ratio of sample particles from the polarization relationship value obtained for the sample particles by the polarization relationship value calculation section and the first relationship information;

a diffusion coefficient acquisition section to acquire a diffusion coefficient of the sample particles;

a second relationship information storage section storing previously determined second relationship information indicating a relationship between the diffusion coefficient, either the major axis length or the minor axis length, and the aspect ratio; and an axis length calculation section to calculate a minor axis length or a major axis length of the sample particles from the aspect ratio calculated by the aspect ratio calculation section, the diffusion coefficient acquired by the diffusion coefficient acquisition section, and the second relationship information.

2. The particle analyzer according to claim 1, wherein the diffusion coefficient acquisition section is configured to acquire a translational diffusion coefficient, and wherein the second relationship information indicates a relationship between the translational diffusion coefficient, either the major axis length or the minor axis length, and the aspect ratio.

3. The particle analyzer according to claim 2, further comprising:

a particle shape determination section to determine whether the sample particles correspond to a spherical particle or aspherical particle according to the polarization relationship value already calculated by the polarization relationship value calculation section, wherein when the particle shape determination section makes a determination that the sample particles correspond to an aspherical particle, the aspect ratio calculation section calculates an aspect ratio of the particles, and the axis length calculation section calculates a minor axis length or a major axis length of the sample particles.

4. The particle analyzer according to claim 3, further comprising:

a particle diameter calculation section to calculate a particle diameter of the sample particles when the particle shape determination section makes a determination that the sample particles correspond to a spherical particle.

5. A particle analysis method comprising the steps of:

irradiating light to a sample having particles being dispersed in a dispersion medium;

detecting two different polarization components contained in scattered light to be caused by the light irradiation;

a polarization relationship value calculation step of calculating a polarization relationship value whose parameter is light intensity of the two polarization components;

obtaining a first relationship information indicating a relationship between the polarization relationship value and an aspect ratio of a major axis length of the particles to a minor axis length thereof, wherein the step of obtaining the first relationship information includes using a standard particle having a known aspect ratio and calculating the polarization relationship value of the known aspect ratio using the two different polarization components of the standard particle obtained using the light source, the polarizing element, and the detector, or obtaining the first relationship information through an external device;

storing, in a first relationship information storage section, the previously determined first relationship information;

an aspect ratio calculation step of calculating the aspect ratio of sample particles from a polarization relationship value obtained by the polarization relationship value calculation step and the first relationship information;

a diffusion coefficient acquisition step of acquiring a diffusion coefficient of the sample particles in the sample;

storing, a second relationship information storage section, previously determined second relationship information indicating a relationship between the diffusion coefficient, either the major axis length or the minor axis length, and the aspect ratio; and an axis length calculation step of calculating a minor axis length or a major axis length of the sample particles from the aspect ratio calculated by the aspect ratio calculation step, the diffusion coefficient acquired by the diffusion coefficient acquisition step, and the second relationship information.

6. A recording medium having recorded therein a particle analysis program used for a particle analyzer configured to irradiate light, using a light source, to a sample having sample particles being dispersed in a dispersion medium and detect, using a polarizing element and a detector, two different polarization components contained in scattered light to be caused by the light irradiation, the particle analysis program causing a computer to have functions as:

a polarization relationship value calculation section to calculate a polarization relationship value whose parameter is light intensity of the two polarization components, the polarization relationship value calculation section being configured to obtain a first relationship information indicating a relationship between the polarization relationship value and an aspect ratio of a major axis length of the particles to a minor axis length thereof, by one of calculating the first relationship information using a standard particle having a known aspect ratio, wherein the polarization relationship value of the known aspect ratio is calculated using the two different polarization components of the standard particle obtained using the light source, the polarizing element, and the detector, or obtaining the first relationship information through an external device, the first relationship information being stored in a first relationship information storage section;

an aspect ratio calculation section to calculate an aspect ratio of a major axis length of the sample particles to a minor axis length of the sample particles from the polarization relationship value obtained by the polarization relationship value calculation section and the first relationship information;
a diffusion coefficient acquisition section to acquire a diffusion coefficient of the sample particles; and
an axis length calculation section to calculate a minor axis length or a major axis length of the sample particles from the aspect ratio calculated by the aspect ratio calculation section, the diffusion coefficient acquired by the diffusion coefficient acquisition section, and second relationship information indicating a relationship between the diffusion coefficient, either the major axis length or the minor axis length, and the aspect ratio, the second relationship information being previously determined and stored in a second relationship information storage section.

* * * * *